(12) United States Patent
Cosmescu

(10) Patent No.: US 11,109,907 B2
(45) Date of Patent: Sep. 7, 2021

(54) ULTRAPOLAR ELECTROSURGERY BLADE AND ULTRAPOLAR ELECTROSURGERY BLADE ASSEMBLY WITH CONDUCTIVE CUTTING EDGES AND TOP AND BOTTOM CONDUCTIVE SURFACES

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 438 days.

(21) Appl. No.: 15/913,569

(22) Filed: Mar. 6, 2018

(65) Prior Publication Data

US 2018/0256243 A1    Sep. 13, 2018

Related U.S. Application Data

(60) Provisional application No. 62/467,739, filed on Mar. 6, 2017, provisional application No. 62/576,213, filed on Oct. 24, 2017.

(51) Int. Cl.
*A61B 18/14* (2006.01)
*A61B 18/04* (2006.01)
(Continued)

(52) U.S. Cl.
CPC ............ *A61B 18/14* (2013.01); *A61B 18/042* (2013.01); *A61B 2018/00589* (2013.01);
(Continued)

(58) Field of Classification Search
CPC ........... A61B 2018/00589; A61B 2018/00601; A61B 2018/00607; A61B 2018/1253;
(Continued)

(56) References Cited

U.S. PATENT DOCUMENTS 4,248,231 A * 2/1981 Herczog ............... A61B 18/14
606/48
4,674,498 A * 6/1987 Stasz ................. A61B 18/1402
604/22

(Continued)

FOREIGN PATENT DOCUMENTS

EP      0280798 A1    9/1988
WO      9940858 A1    8/1999

*Primary Examiner* — Daniel W Fowler
*Assistant Examiner* — Bradford C. Blaise
(74) *Attorney, Agent, or Firm* — Zeman-Mullen & Ford, LLP

(57) ABSTRACT

An ultrapolar electrosurgery blade and an ultrapolar electrosurgery blade assembly. The ultrapolar electrosurgery blade includes top and bottom thin elongated conductive members in vertical alignment and spaced apart from one another along their lengths where each of the top and bottom thin elongated conductive members includes opposing planar sides, a sharp cutting end, and an opposite non-cutting end, and a non-conductive coating covering both opposing sides of the top and bottom thin elongated conductive members and the space located between them where the cutting ends of the elongated conductive members and their opposite non-cutting ends remain exposed. The ultrapolar electrosurgery blade assembly of the present invention having argon beam capability further includes a non-conductive tube member having a hollow tubular shaped opening contained therein and a slot positioned over the top of the
(Continued)

ultrapolar electrosurgery blade and a conductive hollow tubular member contained within at least a portion of the non-conductive tube member.

20 Claims, 10 Drawing Sheets

(51) Int. Cl.
*A61B 18/00* (2006.01)
*A61B 18/12* (2006.01)

(52) U.S. Cl.
CPC ........... *A61B 2018/00601* (2013.01); *A61B 2018/00607* (2013.01); *A61B 2018/1253* (2013.01); *A61B 2018/1412* (2013.01); *A61B 2018/1467* (2013.01)

(58) Field of Classification Search
CPC ...... A61B 2018/126; A61B 2018/1412; A61B 2018/1415; A61B 2018/1467; A61B 18/042; A61B 18/14
See application file for complete search history.

(56) References Cited

U.S. PATENT DOCUMENTS

| | | | |
|---|---|---|---|
| 4,770,067 | A | 9/1988 | Liu et al. |
| 4,850,353 | A * | 7/1989 | Stasz .................. A61B 18/1402 606/45 |
| 4,958,539 | A * | 9/1990 | Stasz .................. A61B 18/1402 204/192.15 |
| 5,125,927 | A | 6/1992 | Belanger |
| 5,281,216 | A | 1/1994 | Klicek |
| 2003/0130655 | A1 | 7/2003 | Woloszko et al. |
| 2006/0241588 | A1 | 10/2006 | Heim et al. |
| 2010/0094283 | A1 | 4/2010 | Cosmescu |
| 2013/0110108 | A1 | 5/2013 | Davison et al. |
| 2013/0331657 | A1 * | 12/2013 | Basson .................. A61B 90/30 600/249 |
| 2014/0257273 | A1 | 9/2014 | Cosmescu |
| 2016/0317209 | A1 | 11/2016 | Cosmescu |
| 2017/0056054 | A1 * | 3/2017 | Dickerson ...... A61B 17/320068 |
| 2017/0319255 | A1 | 11/2017 | Cosmescu |
| 2018/0071011 | A1 | 3/2018 | Cosmescu |

* cited by examiner

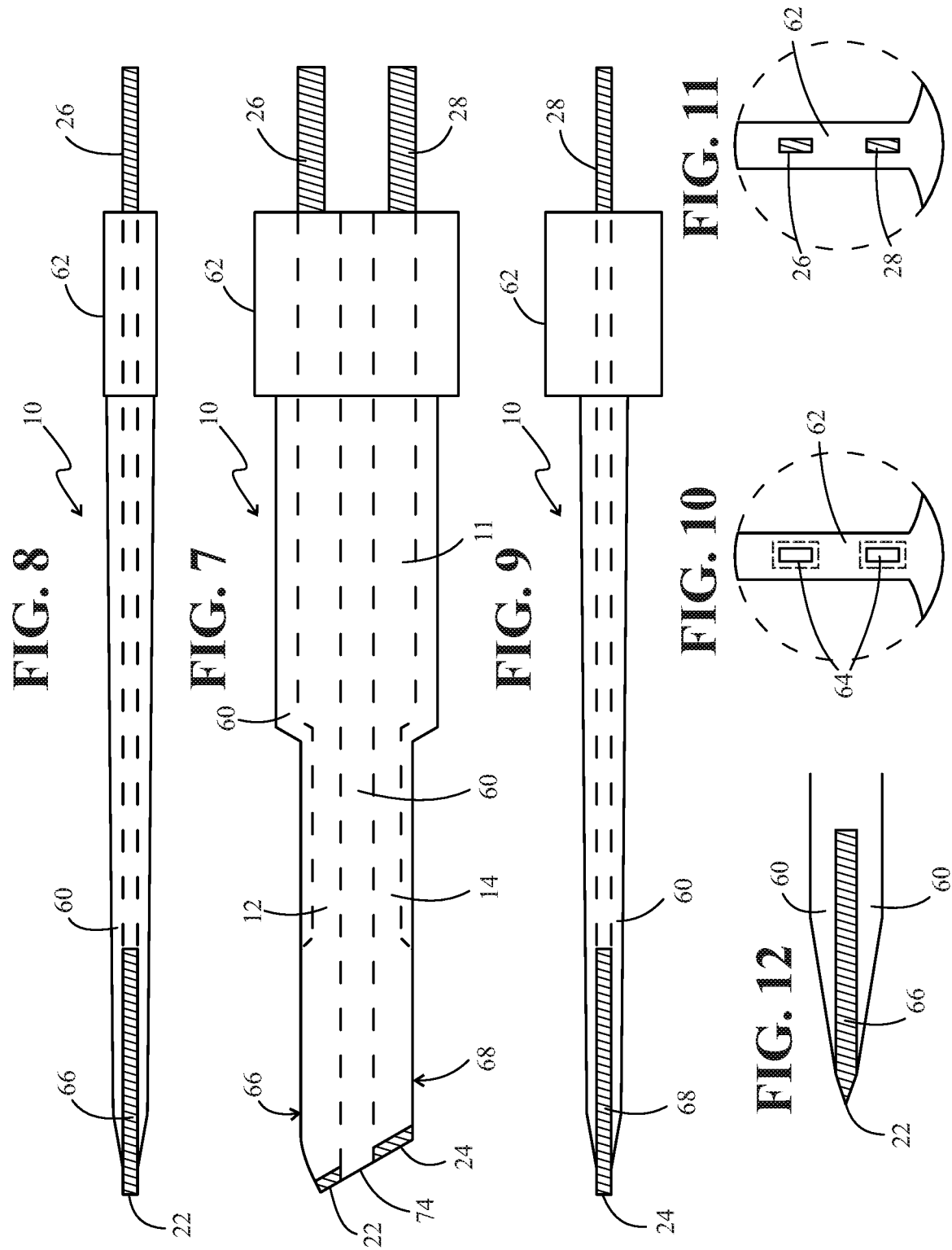

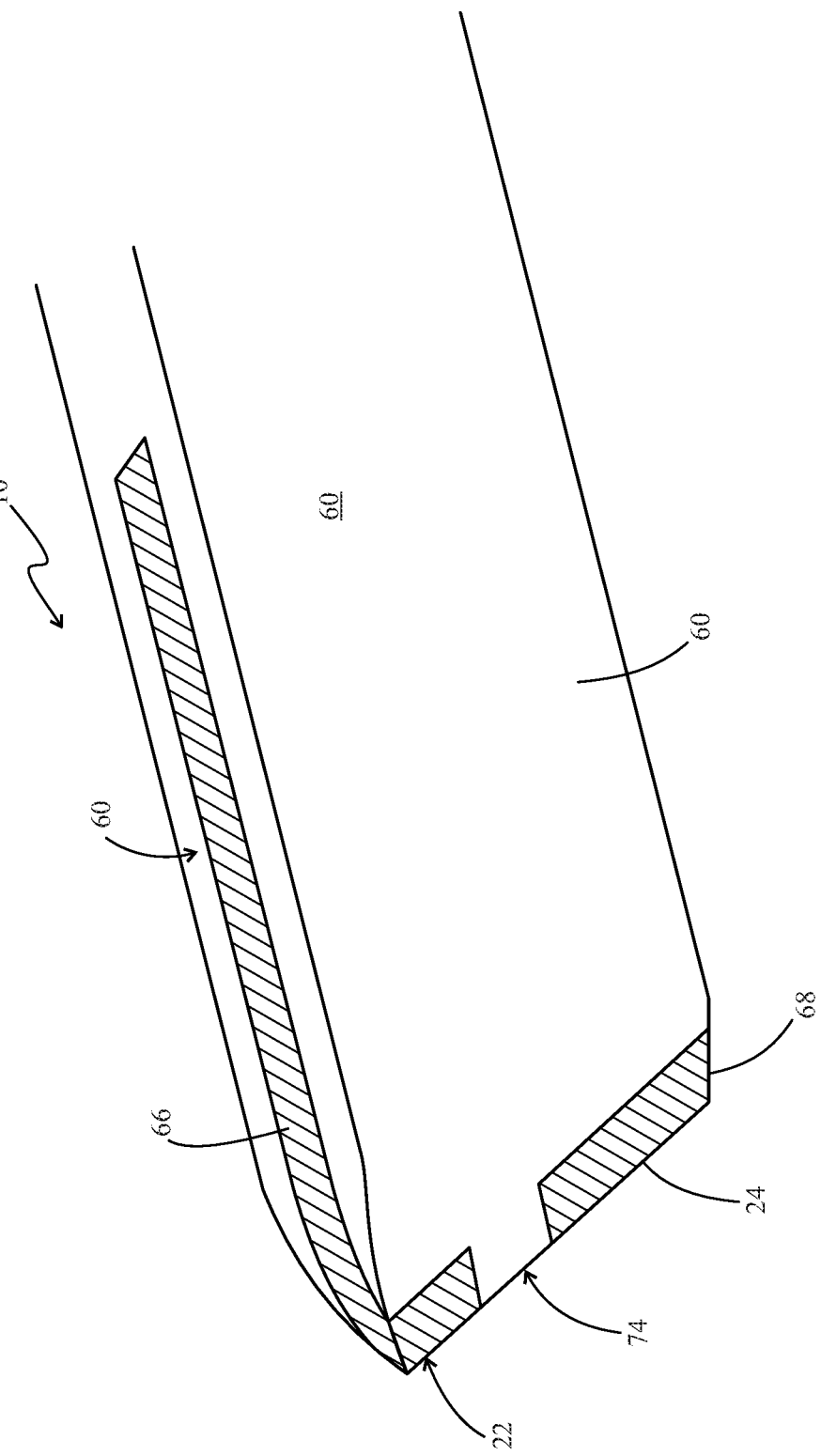

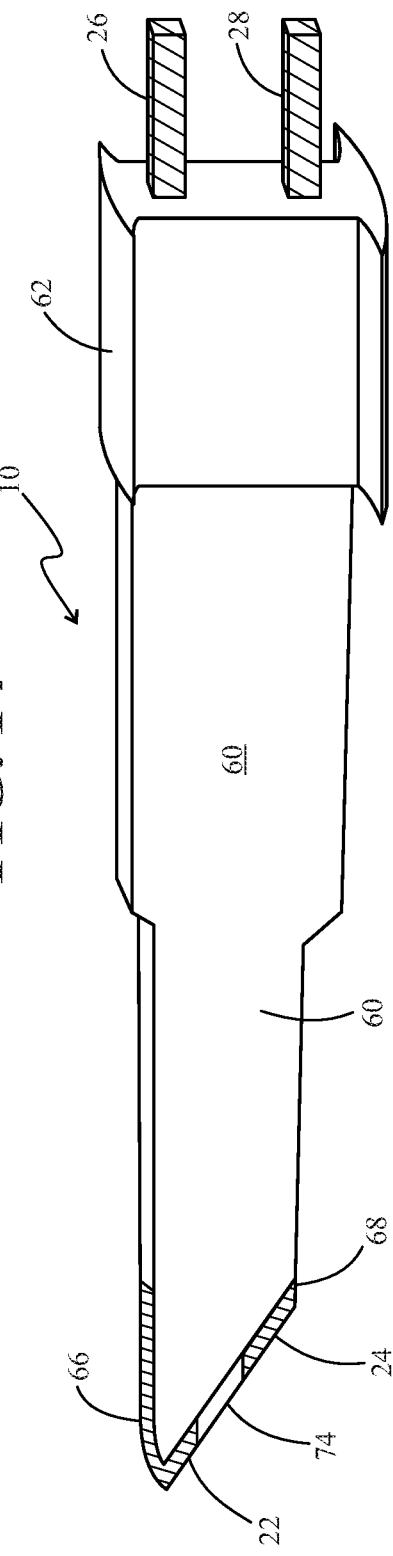
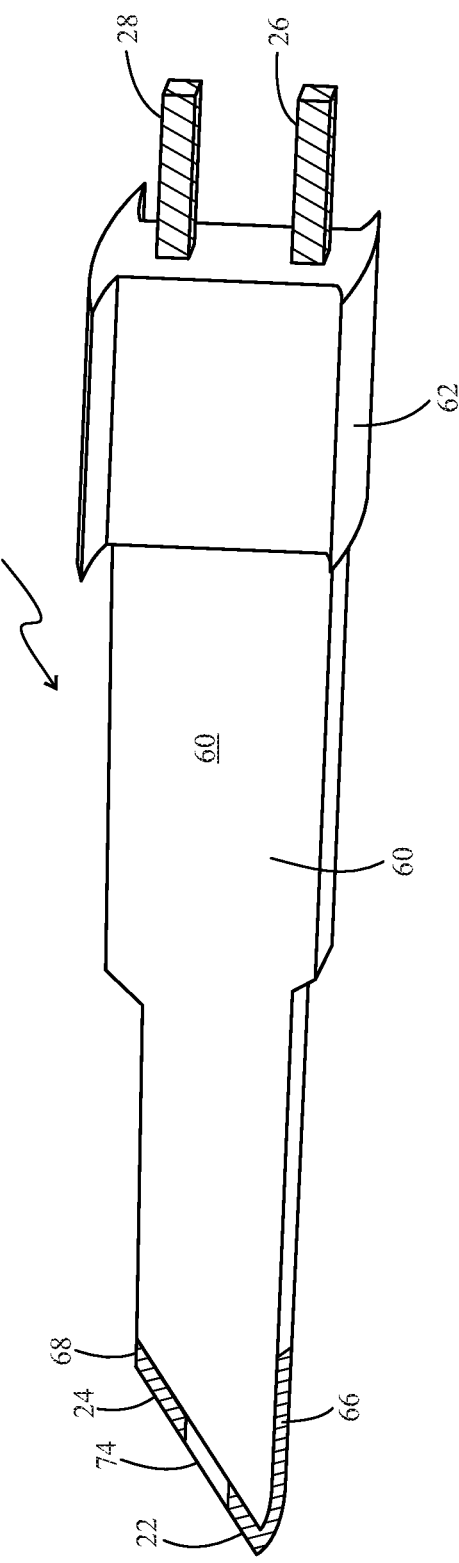

ULTRAPOLAR ELECTROSURGERY BLADE AND ULTRAPOLAR ELECTROSURGERY BLADE ASSEMBLY WITH CONDUCTIVE CUTTING EDGES AND TOP AND BOTTOM CONDUCTIVE SURFACES

CROSS-REFERENCE TO RELATED APPLICATIONS

This application claims priority to provisional patent application having Ser. No. 62/467,739, filed Mar. 6, 2017 and provisional patent application having Ser. No. 62/576,213, filed Oct. 24, 2017, which are herein incorporated by reference in their entireties.

FIELD OF INVENTION

The present invention is generally directed to an ultrapolar electrosurgery blade and an ultrapolar electrosurgery blade assembly which use monopolar energy in a bipolar mode for cutting and coagulation. The ultrapolar electrosurgery blade includes top and bottom thin elongated conductive members in vertical alignment with one another and spaced apart from one another along their lengths wherein each of the top and bottom thin elongated conductive members includes opposing planar sides, a sharp cutting end, and an opposite non-cutting end, and a non-conductive coating covering both opposing sides of the top and bottom thin elongated conductive members and the space located between the top and bottom thin elongated conductive members wherein at least a portion of the cutting ends of the top and bottom thin elongated conductive members and their opposite non-cutting ends remain exposed. During use, one of the top and bottom thin elongated conductive members functions as an active electrode while the other thin elongated conductive member functions as a return electrode. The ultrapolar electrosurgery blade may further include a non-conductive support member/socket having two openings therein in vertical alignment with one another wherein a portion of the top and bottom thin elongated conductive members located near their non-cutting ends are respectively contained within one of the two openings of the support member/socket so that the ultrapolar electrosurgery blade of the present invention can be seated and retained within an electrosurgery pencil. The ultrapolar electrosurgery blade of the present invention is capable of cutting tissue with the sharp conductive cutting ends of the blade without using RF energy as well as cutting tissue with the sharp non-conductive cutting end/edge that is located between the sharp conductive cutting ends. In addition, the ultrapolar electrosurgery blade of the present invention is capable of coagulating tissue and/or enhanced cutting of tissue by supplying low power to the ultrapolar electrosurgery blade, and simultaneously cutting and coagulating tissue by cutting tissue with the sharp cutting ends of the ultrapolar electrosurgery blade while coagulating tissue by applying low power to the ultrapolar electrosurgery blade.

The present invention is also directed to an ultrapolar electrosurgery blade assembly with argon beam capability which includes the previously described ultrapolar electrosurgery blade, a non-conductive tube member having a hollow tubular shaped opening contained therein and a slot where the slot is positioned over the top of the ultrapolar electrosurgery blade, and a conductive hollow tubular member contained within at least a portion of the non-conductive tube member. Conductive projections may extend from the conductive hollow tubular member and/or a portion of the top thin elongated conductive member that is exposed depending on the type of coagulation to be performed such as argon plasma coagulation alone and/or argon plasma assisted coagulation. The non-conductive coating is a continuous coating that also fills any space located between the sharp cutting ends of the top and bottom thin elongated conductive members to create a sharp non-conductive cutting end of the ultrapolar electrosurgery blade located between the sharp conductive cutting ends of the top and bottom thin elongated conductive members. The conductive hollow tubular member contained within the non-conductive tube member may also include a slot that is positioned over a top portion of the ultrapolar electrosurgery blade. The ultrapolar electrosurgery blade assembly with argon beam capability provides argon plasma coagulation of tissue and/or argon plasma assisted cutting and/or argon plasma assisted coagulation of tissue depending on the location and configuration of the active and return electrodes of the ultrapolar electrosurgery blade.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monpolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy and thereby reduces or eliminates the likelihood of tissue damage and sparking associated with monopolar electrosurgery, it has limited ability to cut and coagulate large bleeding areas.

Since surgical tools and devices currently available to surgeons require switching between cutting and coagulation modes during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade having a sharp edge for cutting and RF for coagulation would meet this need. The ultrapolar electrosurgery blade of the present invention which uses monopolar energy in a bipolar mode has sharp cutting edges made of a hard conductive material, such as stainless steel, tungsten, etc. that are separated by a sharp non-conductive cutting edge that can all be used for precisely cutting tissue without the use of any RF energy. However, RF energy can also be used with the ultrapolar electrosurgery blade of the present invention for coagulation. When low voltage is used to supply power to the ultrapolar electrosurgery blade of the present invention for coagulation, the sharp cutting edges of the ultrapolar electrosurgery blade can simultaneously be used for cutting without the need to provide higher voltage to the ultrapolar electrosurgery blade to carry out the cutting. Therefore, there is no need to switch over to a cutting mode to perform cutting and instead both cutting and coagulation can be performed simultaneously at low power levels supplied from the generator.

Moreover, the low power used to employ the ultrapolar electrosurgery blade of the present invention for both cutting and coagulation substantially reduces the damage to the lateral tissue and the tissue will not stick to the ultrapolar blade. Further, since the ultrapolar electrosurgery blade of the present invention includes top and bottom conductive members/electrodes that are both attached to the generator, only a very small amount of a patient's tissue located between the electrodes or adjacent to the electrodes is included in the circuit thereby eliminating the risk of current diversion to other parts of the patient that can occur in monopolar systems where the entire patient is in the circuit.

It is also common to use argon beam coagulators during electrosurgery. In argon beam coagulation (ABC), plasma is applied to tissue by a directed beam of ionized argon gas (plasma) which causes a uniform and shallow coagulation surface thereby stopping blood loss. In some instances, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as making incisions in tissue by cutting, or stopping the bleeding at the surgical site.

Since surgical tools and devices currently available to surgeons require switching between cutting and argon beam coagulation during the surgical procedure, there is a need for a surgical device or tool that enables a surgeon or user to utilize the best methods used for cutting and cessation of bleeding at the surgical site at the same time, or simultaneously, in addition to being able to use them separately. An ultrapolar electrosurgery blade having a sharp edge for cutting and argon beam capability for capsulation would meet this need. The ultrapolar electrosurgery blade assembly of the present invention with a sharp cutting edge and argon beam capability enables a user or surgeon to perform cutting and coagulation without the need to switch between cutting and coagulation modes. There is also a need for an electrosurgical device that enables a user or surgeon to choose from a number of different separate or combined tissue cutting and coagulation methods since different methods may work best depending on the surgical procedure and circumstances that present themselves during surgery.

The ultrapolar electrosurgery blade assembly with argon beam capability of the present invention is capable of coagulating a patient's tissue using argon plasma alone without contacting the patient's tissue (i.e. non-contact argon beam coagulation). In this embodiment of the ultrapolar electrosurgery blade assembly, an exposed portion of the return electrode of the ultrapolar electrosurgery blade is positioned near the top of the electrosurgey blade such that it is in alignment with the conductive hollow tubular member through which the argon gas is introduced and the conductive protection extending from an end of the conductive tube member so that a complete circuit is formed to ionize the argon gas for argon plasma coagulation. The ultrapolar electrosurgery blade assembly of the present invention is also capable of cutting a patient's tissue using the sharp cutting edge (comprising both conductive and non-conductive materials) of the ultrapolar blade alone without any use of RF energy and without any use of argon plasma. The ultrapolar electrosurgery blade assembly of the present invention can also enhance the cutting of a patient's tissue using the sharp conductive cutting edges of the ultrapolar blade by also supplying RF energy to the ultrapolar electrosurgery blade. Moreover, the ultrapolar electrosurgery blade assembly of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar blade can be used without any RF energy for cutting while the conductive tube through which the argon gas is introduced, and which is contained within the non-conductive tube, is activated and directed to provide ionized argon gas for argon plasma coagulation of tissue. In another example, low power may be applied to the ultrapolar blade to coagulate tissue or enhance cutting of tissue while the conductive tube through which the argon gas is introduced, and which is contained within the non-conductive tube, is activated and directed to provide ionized argon gas for argon plasma coagulation of tissue.

Both the ultrapolar electrosurgery blade of the present invention and the ultrapolar electrosurgery blade assembly having argon beam capability of the present invention could be used with an electrosurgery handpiece/pencil with smoke evacuation capability or an electrosurgery handpiece/pencil without smoke evacuation capability. Both the ultrapolar electrosurgery blade of the present invention and the ultrapolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. In instances where tissue cutting and coagulation are performed at the same time without switching between modes or methods, operating time is decreased and the lateral damage to the tissue is reduced or eliminated. Further, use of monopolar energy in a bipolar mode with the ultrapolar electrosurgery blade of the present invention and the ultrapolar electrosurgery blade assembly with argon beam capability of the present invention essentially eliminates the risk of current diversion that can occur in monopolar systems. In addition, performing both tissue cutting and coagulation at the same time along with smoke evacuation will protect the surgeon and staff from inhaling smoke and particles. It will also enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to an ultrapolar electrosurgery blade which uses monopolar energy in a bipolar mode and which includes top and bottom thin elongated conductive members in vertical alignment with one another and spaced apart from one another along their lengths wherein each of the top and bottom thin elongated conductive members includes opposing planar sides, a sharp cutting end for cutting, and an opposite non-cutting end, and a non-conductive coating covering both opposing planar sides of the top and bottom thin elongated conductive members and the space located between them wherein the cutting ends of the thin elongated conductive members and their opposite non-cutting ends remain exposed. During use, one of the top and bottom thin elongated conductive members functions as an active electrode while the other thin elongated conductive member functions as a return electrode. The ultrapolar electrosurgery blade may further include a non-conductive support member/socket having two openings therein positioned in vertical alignment with one another wherein a portion of each of the top and bottom thin elongated conductive members located near their non-cutting ends are respectively contained within one of the two openings of the support member/socket so that the ultrapolar electrosurgery blade of the present invention can be seated and retained within an electrosurgery pencil.

The top and bottom thin elongated conductive members may be formed from a single thin conductive member having vertically aligned top and bottom elongated conductive members spaced apart from one another along their lengths with each having a separate sharp cutting end at one end and a non-cutting end at their opposite ends where their non-cutting ends are joined. The non-conductive coating may then be applied to the single thin conductive member (which includes the top and bottom elongated conductive members and the space located between the top and bottom elongated conductive members) to form an electrosurgery blade where at least a portion of the cutting ends of the top and bottom elongated conductive members and their joined opposing non-cutting ends remain exposed and not covered by the non-conductive coating. The joined non-cutting ends of the top and bottom elongated conductive members can then be removed to produce separately exposed and unconnected non-cutting ends for the top and bottom elongated conductive members which can be respectively inserted into a non-conductive support member/socket having two openings (as described above). One advantage in forming the ultrapolar electrosurgery blade of the present invention using a single thin conductive member having vertically aligned top and bottom elongated conductive members spaced apart from one another along their lengths with separate sharp cutting ends at one end and joined opposite non-cutting ends where the joined ends are later removed to produce separate non-cutting ends is that it facilitates the construction and production of the ultrapolar electrosurgery blade by providing a unitary component for creating separate elements of the blade thereby increasing the consistency and accuracy of the blades. Another advantage of this type of formation of the ultrapolar electrosurgery blades are the increased efficiencies in the production of the blades and the reduction in production costs. Still another advantage of this type of blade formation for the ultrapolar electrosurgery blade of the present invention is that it enhances the strength of the blade as well as the proper functioning of the blade.

In one exemplary embodiment of the ultrapolar electrosurgery blade of the present invention, the non-conductive coating covers at least a portion of the top of the top thin elongated conductive member and at least a portion of the bottom of the bottom thin elongated conductive member. The non-conductive coating may be a continuous coating that also fills in any space located between the sharp cutting ends of the top and bottom thin elongated conductive members. In another exemplary embodiment of the ultrapolar electrosurgery blade of the present invention, a portion of the top of the top thin elongated conductive member is exposed between portions of the non-conductive coating located on the top of the electrosurgery blade and a portion of the bottom of the bottom thin elongated conductive member is exposed between portions of the non-conductive coating located on the bottom of the electrosurgery blade. The ultrapolar electrosurgery blade of the present invention may have a sharp cutting edge that is comprised of the sharp cutting ends of the top and bottom thin elongated conductive members separated by a sharp non-cutting end comprised of the non-conductive coating.

The top and bottom thin elongated conductive members (as well as the single thin conductive member that the top and bottom elongated members may be formed from) may comprise a hard metal such as, for example, stainless steel, titanium, and/or tungsten. The non-conductive coating of the ultrapolar electrosurgery blade of the present invention and the non-conductive support member may be comprised of a ceramic material.

The ultrapolar electrosurgery blade of the present invention which uses monopolar energy in a bipolar mode has sharp cutting edges made of a hard conductive material, such as stainless steel, tungsten, etc. that are separated by a sharp non-conductive cutting edge that can all be used for precisely cutting tissue without the use of any RF energy. However, RF energy can also be used with the ultrapolar electrosurgery blade of the present invention for coagulation. When low voltage is used to supply power to the ultrapolar electrosurgery blade of the present invention for coagulation, the sharp cutting edges of the ultrapolar electrosurgery blade can simultaneously be used for cutting without the need to provide higher voltage to the ultrapolar electrosurgery blade to carry out the cutting. Therefore, there is no need to switch over to a cutting mode to perform cutting and instead both cutting and coagulation can be performed simultaneously at low power levels supplied front the generator.

The ultrapolar electrosurgery blade assembly of the present invention having argon beam capability includes the ultrapolar electrosurgery blade described above and further includes a non-conductive tube member having a hollow tubular shaped opening contained therein and a slot where the slot is positioned over the top of the ultrapolar electrosurgery blade, and a conductive hollow tubular member contained within at least a portion of the non-conductive tube member. In one exemplars embodiment of the ultrapolar electrosurgery blade assembly of the present invention, a portion of the top of the top thin elongated conductive member is exposed between portions of the non-conductive coating located on the top of the ultrapolar electrosurgery blade and contained within the non-conductive tube member and the ultrapolar electrosurgery blade assembly further includes a conductive projection extending from the conductive hollow tubular member contained within the non-conductive tube member and/or the portion of the top of the top thin elongated conductive member located on top of the electrosurgery blade and contained within the non-conductive tube member. In another exemplary embodiment of the ultrapolar electrosurgery blade assembly of the present invention, the non-conductive coating covers the top of the top thin elongated conductive member located between the conductive hollow tubular member and the exposed cutting end of the top thin elongated conductive member and the ultrapolar electrosurgery blade assembly further includes a conductive projection extending from an end of the conductive hollow tubular member contained within the non-conductive tube member.

The conductive hollow tubular member contained within the non-conductive tube member may include a slot that, like the slot in the non-conductive tube member, is also positioned over at least a portion of the top of the ultrapolar electrosurgery blade. Like the top and bottom thin elongated conductive members of the ultrapolar electrosurgery blade, the conductive hollow tubular member, as well as the conductive projections, may comprise a hard metal such as, for example, stainless steel, titanium, and/or tungsten. Further, like the non-conductive coating of the ultrapolar electrosurgery blade, the non-conductive tube member may be comprised of a ceramic material.

The ultrapolar electrosurgery blade assembly with argon beam capability of the present invention is capable of coagulating a patient's tissue using argon plasma alone without contacting the patient's tissue (i.e. non-contact argon beam coagulation). In this embodiment of the ultrapolar electrosurgery blade assembly, an exposed portion of the return electrode of the ultrapolar electrosurgery blade is positioned near the top of the electrosurgery blade such that it is in alignment with the conductive hollow tubular member through which the argon gas is introduced and the conductive projection extending from an end of the conductive tube member so that a complete circuit is formed to ionize the argon gas for argon plasma coagulation. The ultrapolar electrosurgery blade assembly of the present invention is also capable of cutting a patient's tissue using the sharp cutting edge (comprising both conductive and non-conductive materials) of the ultrapolar blade alone without any use of RF energy and without any use of argon plasma. The ultrapolar electrosurgery blade assembly of the present invention can also enhance the cutting of a patient's tissue using the sharp conductive cutting edges of the ultrapolar blade by also supplying RF energy to the ultrapolar electrosurgery blade. Moreover, the ultrapolar electrosurgery blade assembly of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp culling edge of the ultrapolar blade can be used without any RF energy for cutting while the conductive tube through which the argon gas is introduced, and which is contained within the non-conductive tube, is activated and directed to provide ionized argon gas for argon plasma coagulation of tissue. In another example, low power may be applied to the ultrapolar blade to coagulate tissue or enhance cutting of tissue while the conductive tube through which the argon gas is introduced, and which is contained within the non-conductive tube, is activated and directed to provide ionized argon gas for argon plasma coagulation of tissue.

BRIEF DESCRIPTION OF THE DRAWINGS

FIG. 7 is an external side view showing the exemplary embodiment of the ultrapolar electrosurgery blade shown in FIG. 3 with the joined portion of the non-cutting ends of the top and bottom elongated conductive members removed and the top and bottom elongated conductive members covered by the non-conductive coating shown in phantom;

FIG. 8 is a top view of the exemplary embodiment of the ultrapolar electrosurgery blade of the present invention shown in FIG. 7 with the top elongated conductive member covered by the non-conductive coating shown in phantom;

FIG. 9 is a bottom view of the exemplary embodiment of the ultrapolar electrosurgery blade of the present invention shown in FIG. 7 with the bottom elongated conductive member covered by the non-conductive coating shown in phantom;

FIG. 10 is a front end view of an exemplary embodiment of a support member/connector member into which unconnected non-cutting ends of the top and bottom elongated conductive members of the ultrapolar electrosurgery blade are placed so that the ultrapolar electrosurgery blade of the present invention can be connected to, and unconnected or removed from, an electrosurgery pencil;

FIG. 11 is an end view of the support member/connector member shown in FIG. 10 showing conductive unconnected non-cutting ends of the ultrapolar electrosurgery blade of the present invention retained within the openings in the support member/connector member;

FIG. 12 is a partial top view of another exemplary embodiment of the ultrapolar electrosurgery blade of the present invention showing a sharp cutting end beveled on both sides to create a sharp cutting tip;

FIG. 13 is a partial perspective view of the exemplary embodiment of the ultrapolar electrosurgery blade of the present invention shown in FIGS. 3 and 7;

FIGS. 14 and 15 are opposing perspective side views of the exemplary embodiment of the ultrapolar electrosurgery blade of the present invention shown in FIG. 7 to further reveal the shape of the ultrapolar electrosurgery blade of the present invention;

DETAILED DESCRIPTION OF EXEMPLARY EMBODIMENTS

Figure 1:
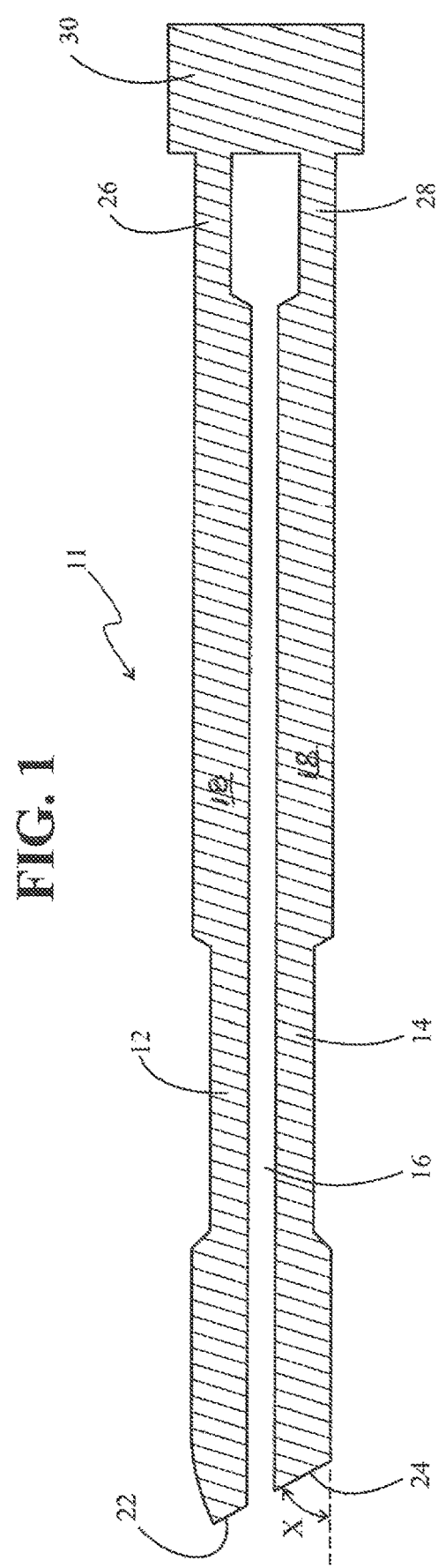
FIG. 1 is a side view of an exemplary embodiment of a thin conductive member having top and bottom thin elongated conductive members used to make the ultrapolar electrosurgery blade of the present invention.

The exemplary embodiments of the ultrapolar electrosurgery blade and ultrapolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. The ultrapolar electrosurgery blade of the present invention is capable of cutting tissue with the sharp conductive cutting ends of the blade without using RF energy as well as cutting tissue with the sharp non-conductive cutting end/edge that is located between the sharp conductive cutting ends. In addition, the ultrapolar electrosurgery blade of the present invention is capable of coagulating tissue and/or enhanced cutting of tissue by supplying very low power, such as 5 to 15 watts, to the ultrapolar electrosurgery blade, and simultaneously cutting and coagulating tissue by cutting tissue with the sharp cutting ends of the ultrapolar electrosurgery blade while coagulating tissue by applying very low power to the ultrapolar electrosurgery blade.

The ultrapolar electrosurgery blade assembly of the present invention with a sharp cutting edge and argon beam capability enables a user or surgeon to perform cutting and coagulation without the need to switch between cutting and coagulation modes. There is also a need for an electrosurgical device that enables a user or surgeon to choose from a number of different separate or combined tissue cutting and coagulation methods since different methods may work best depending on the surgical procedure and circumstances that present themselves during surgery. The ultrapolar electrosurgery blade assembly with argon beam capability of the present invention is capable of coagulating a patient's tissue using argon plasma alone without contacting the patient's tissue (i.e. non-contact argon beam coagulation). The ultrapolar electrosurgery blade assembly of the present invention is also capable of cutting a patient's tissue using the sharp cutting edge (comprising both conductive and non-conductive materials) of the ultrapolar blade alone without any use of RF energy and without any use of argon plasma. The ultrapolar electrosurgery blade assembly of the present invention can also enhance the cutting of a patient's tissue using the sharp conductive cutting edges of the ultrapolar blade by also supplying RF energy to the ultrapolar electrosurgery blade. Moreover, the ultrapolar electrosurgery blade assembly of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar blade can be used without any RF energy for cutting while the conductive tube through which the argon gas is introduced, and which is contained within the non-conductive tube, is activated and directed to provide ionized argon gas for argon plasma coagulation of tissue. In another example, low power may be applied to the ultrapolar blade to coagulate tissue or enhance cutting of tissue while the conductive tube through which the argon gas is introduced, and which is contained within the non-conductive tube, is activated and directed to provide ionized argon gas for argon plasma coagulation of tissue.

The identity of the elements/features that relate to the numbers shown in the drawing figures are as follows:

10 ultrapolar electrosurgery blade
11 thin conductive member
12 top thin elongated conductive member
14 bottom thin elongated conductive member
16 elongated space between top and bottom thin elongated conductive members
18 opposing planar sides (of top and bottom thin elongated conductive members)
22 sharp cutting end of top thin elongated conductive member
24 sharp cutting end of bottom thin elongated conductive member
26 opposite non-cutting end of top thin elongated conductive member
28 opposite non-cutting end of bottom thin elongated conductive member
30 portion of thin conductive member joining opposite non-cutting ends of top and bottom thin elongated conductive members 26 and 28
31 thin conductive member
32 top thin elongated conductive member
34 bottom thin elongated conductive member
36 elongated space between top and bottom thin elongated conductive members
38 opposing planar sides (of top and bottom thin elongated conductive members)
42 sharp cutting end of top thin elongated conductive member
44 sharp cutting end of bottom thin elongated conductive member
46 opposite non-cutting end of top thin elongated conductive member
48 opposite non-cutting end of bottom thin elongated conductive member
50 portion of thin conductive member joining opposite non-cutting ends of top and bottom thin elongated conductive members 46 and 48
60 non-conductive coating/housing
62 non-conductive support member/socket/connecting member
63 rounded top portion (of non-conductive support member/socket/connecting member)
65 rounded bottom portion (of non-conductive support member/socket/connecting member)
64 two vertically aligned openings
66 top of the top thin elongated conductive member
68 bottom of the bottom thin elongated conductive member
70 sharp non-conductive cutting end
72 non-conductive support member/socket/connecting member for ultrapolar telescopic electrosurgery pencil 73 rounded top portion (of non-conductive support member/socket/connecting member for ultrapolar telescopic electrosurgery pencil)
74 two vertically aligned openings
100 ultrapolar electrosurgery blade assembly
120 non-conductive tube member
122 hollow tubular shaped opening (of non-conductive tube member)
124 slot (of non-conductive tube member)
130 conductive hollow tubular member
132 conductive projection
200 ultrapolar electrosurgery blade assembly
220 non-conductive tube member
222 hollow tubular shaped opening (of non-conductive tube member)
224 slot (of non-conductive tube member)
230 conductive hollow tubular member
232 conductive projection
300 ultrapolar electrosurgery blade assembly
320 non-conductive tube member
322 hollow tubular shaped opening (of non-conductive tube member)
324 slot (of non-conductive tube member)
330 conductive hollow tubular member
332 conductive projection
334 slot (of conductive hollow tubular member)

FIG. 1 is a side view of an exemplary embodiment of a thin conductive member 11 having top and bottom thin elongated conductive members 12, 14 used to make the ultrapolar electrosurgery blade 10 of the present invention. Thin conductive member 11 includes a top thin elongated conductive member 12 and a bottom thin elongated conductive member 14 in vertical alignment with one another and separated from one another along their lengths by a space 16. The width of the space 16 located between the top thin elongated conductive member 12 and the bottom thin elongated conductive member 14 is the same along more than half the length of the top and bottom thin elongated conductive members 12, 14. The top and bottom elongated conductive members 12, 14 each have opposing planar sides 18 with each opposing planar side 18 having a length and a width, a sharp cutting end 22, 24 and an opposite non-cutting end 26, 28 where the opposite non-cutting ends 26, 28 are joined by a portion 30 of the thin conductive member 11. The width of the space 16 that is the same along more than half the length of the top and bottom thin elongated conductive members 12, 14 is smaller than the width of each of the opposing planar sides 18 of the top and bottom thin elongated conductive members 12, 14 located adjacent to the sharp cutting ends 22, 24. The width of the space 16 that is the same along more than half the length of the top and bottom thin elongated conductive members 12, 14 is also smaller than the width of each of the opposing planar sides 18 located at a middle of the length of the top and bottom thin elongated conductive members 12, 14. In one exemplary, embodiment of the thin conductive member 11, the sharp cutting ends 22, 24 of the thin conductive member 11 form an angle X relative to a plane that is in horizontal alignment with the bottom of the bottom thin elongated conductive member 14 where X is a sixty degree angle.

Figure 2:
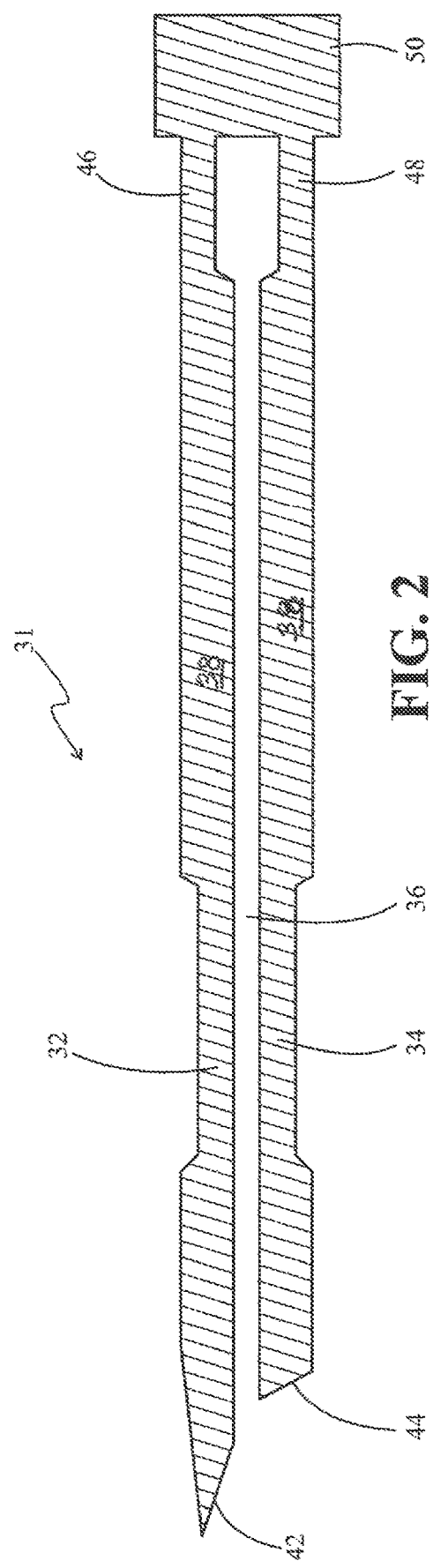
FIG. 2 is a side view of another exemplary embodiment of a thin conductive member having top and bottom thin elongated conductive members used to make the ultrapolar electrosurgery blade of the present invention.
Figure 4:
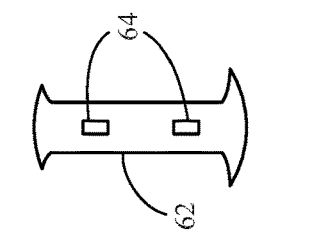
FIG. 4 is a front end view of a support member/socket/connector member which retains a portion of the unconnected non-cutting ends of the top and bottom elongated conductive members of the ultrapolar electrosurgery blade thereby facilitating the connection of the ultrapolar electrosurgery blade of the present invention to an electrosurgery pencil.

A side view of another exemplary embodiment of a thin conductive member 31 having top and bottom thin elongated conductive members 32, 34 used to make the ultrapolar electrosurgery blade 10 of the present invention is shown in FIG. 2, Like the thin conductive member 11 shown in FIG. 1, thin conductive member 31 includes a top thin elongated conductive member 32 and a bottom thin elongated conductive member 34 in vertical alignment with one another and separated from one another along their lengths by a space 36. The width of the space 36 located between the top thin elongated conductive member 32 and the bottom thin elongated conductive member 34 is the same along: more than half the length of the top and bottom thin elongated conductive members 32, 34. The top and bottom elongated conductive members 32, 34 each have opposing planar sides 38 with each opposing planar side 38 having a length and a width, a sharp cutting end 42, 44 and an opposite non-cutting end 46, 48 where the opposite non-cutting ends 46, 48 are joined by a portion 50 of the thin conductive member 31. The width of the space 36 that is the same along more than half the length of the top and bottom thin elongated conductive members 32, 34 is smaller than the width of each of the opposing planar sides 38 of the top and bottom thin elongated conductive members 32, 34 located adjacent to the sharp cutting ends 42, 44. The width of the space 36 that is the same along more than half the length of the top and bottom thin elongated conductive members 32, 24 is also smaller than the width of each of the opposing planar sides 38 located at a middle of the length of the top and bottom thin elongated conductive members 32, 34. As shown in FIG. 2, the sharp cutting end 42 of top thin elongated conductive member 32 extends well beyond the sharp cutting end 44 of the bottom thin elongated conductive member 34 and the angle of the sharp cutting end 44 in relation to the bottom of the bottom thin elongated conductive member 34 is much steeper than the angle of the sharp cutting end 42 in relation to the bottom of the top thin elongated conductive member 32. It will be understood by those skilled in the art that the sharp cutting ends of the top and bottom thin elongated conductive members of the ultrapolar electrosurgery blade may include any number of shapes and/or configurations depending on the type and circumstances of the surgical procedure to be performed using the ultrapolar electrosurgery blade.

Figure 5:
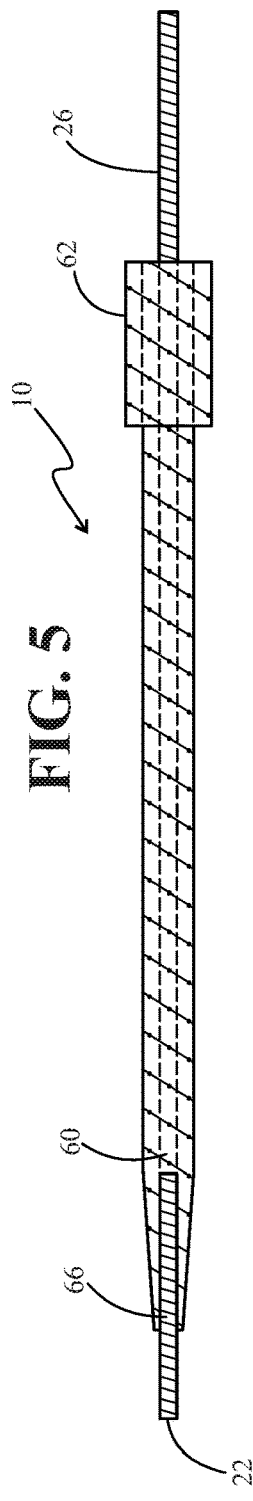
FIG. 5 is a top view of the exemplary embodiment of the ultrapolar electrosurgery blade of the present invention shown in FIG. 3 with the thin conductive member shown in phantom.
Figure 3:
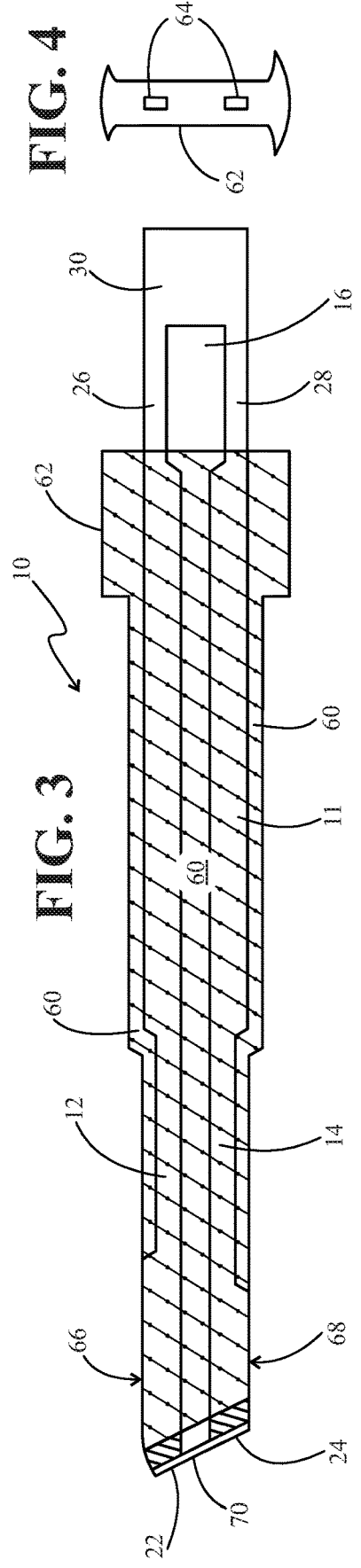
FIG. 3 is side perspective view of an exemplary embodiment of the ultrapolar electrosurgery blade of the present invention showing the exemplary embodiment of the thin conductive member of FIG. 1 coated with a non-conductive coating except for the cutting ends and the joined non-cutting ends of the top and bottom elongated conductive members where the non-conductive coating is represented by light shade hash marks and/or hash marks made of unconnected dots.
Figure 6:
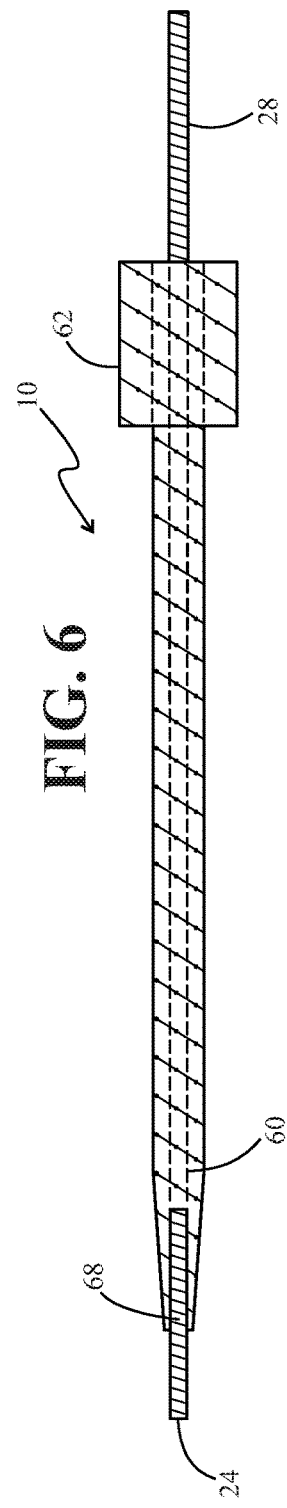
FIG. 6 is a bottom view of the exemplary embodiment of the ultrapolar electrosurgery blade of the present invention shown in FIG. 3 with the thin conductive member shown in phantom.

FIG. 3 is side perspective view of an exemplary embodiment of the ultrapolar electrosurgery blade 10 of the present invention showing the exemplary embodiment of the thin conductive member 11 of FIG. 1 coated with a non-conductive coating 60 except for the cutting ends 22, 24 and the joined non-cutting ends 26, 28, 30 of the top and bottom elongated conductive members 12, 14 where the non-conductive coating 60 is represented by light shade hash marks and/or hash marks made of unconnected dots. FIG. 5 is a top view of the exemplary embodiment of the ultrapolar electrosurgery blade 10 of the present invention shown in FIG. 3 with the thin conductive member 11 shown in phantom and FIG. 6 is a bottom view of the exemplary embodiment of the ultrapolar electrosurgery blade 10 of the present invention shown in FIG. 3 with the thin conductive member 11 shown in phantom. As can be seen from FIGS. 3 and 5-6, the non-conductive coating 60 covers the thin conductive member 11 except for sharp cutting ends 22, 24 of the top and bottom elongate conductive members 12, 14, a portion of the top 66 of the of the top elongated conductive member 12, a portion of the bottom 68 of the bottom elongated conductive member 14, the non-cutting ends 26, 28 of the top and bottom elongated conductive members 12, 14 and the portion 30 of the thin conductive member 11 that joins the non-cutting ends 26, 28.

After the non-conductive coating 60 is applied to the thin conductive member 11 and the coating 60 is set, the portion 30 that joins the non-cutting ends 26, 28 is removed as shown in FIG. 7 to provide an ultrapolar electrosurgery blade 10 having unconnected conductive non-cutting ends 26, 28 supported by a support member/socket/connecting member 64 which facilitates connection of the ultrapolar electrosurgery blade 10 of the present invention to an electrosurgery pencil. FIG. 7 is an external side view showing the exemplary embodiment of the ultrapolar electrosurgery blade 10 shown in FIG. 3 with the joined portion 30 of the non-cutting ends 26, 28 of the top and bottom elongated conductive members 12, 14 removed and most of the top and bottom elongated conductive members 12, 14 covered by the non-conductive coating 60 shown in phantom. Advantages in forming the ultrapolar electrosurgery blade 10 of the present invention using a single thin conductive member 11 having vertically aligned top and bottom elongated conductive members 12, 14 spaced apart from one another along their lengths with separate sharp cutting ends 22, 24 at one end and joined opposite non-cutting ends 26, 28, 30 where the joined ends are later removed to produce separate non-cutting ends 26, 28 include 1) facilitation of the construction and production of the ultrapolar electrosurgery blade of the present invention by providing a unitary component for creating separate elements of the blade thereby increasing the consistency and accuracy of the blades, 2) increased efficiencies in the production of the blades and the reduction in production costs, and 3) enhanced strength of the blade as well as the enhanced proper functioning of the blade.

FIG. 8 is a top view of the exemplary embodiment of the ultrapolar electrosurgery blade 10 of the present invention shown in FIG. 7 with the top elongated conductive member 12 that is covered by the non-conductive coating 60 shown in phantom. A portion of the top 66 of the top elongated conductive member 12 is exposed between portions of non-conductive coating 60 located on a top of the ultrapolar electrosurgery blade. FIG. 9 is a bottom view of the exemplary embodiment of the ultrapolar electrosurgery blade 10 of the present invention shown in FIG. 7 with the bottom elongated conductive member 14 covered by the non-conductive coating 60 shown in phantom. A portion of the bottom 68 of the bottom elongated conductive member 14 is exposed between portions of non-conductive coating 60 located on a bottom of the ultrapolar electrosurgery blade.

Further, as shown in FIG. 7, the non-conductive coating is a continuous coating that fills elongated space 16 located between the top and bottom elongated conductive members 12, 14 as well as any space located between the sharp cutting ends 22, 24 of the top and bottom elongated conductive members 12, 14. The space between the sharp cutting ends 22, 24 of the top and bottom elongated conductive members 12, 14 that is filled with the non-conductive coating 60 forms a sharp non-conductive cutting end positioned between the sharp conductive cutting ends 22, 24 of the ultrapolar electrosurgery pencil 10.

FIG. 10 is a front end view of an exemplary embodiment of a support member/socket/connector member 62 into which unconnected non-cutting ends 26, 28 of the top and bottom elongated conductive members 12, 14 of the ultrapolar electrosurgery blade 10 are placed so that the ultrapolar electrosurgery blade 10 of the present invention can be easily connected to, and unconnected or removed from, an electrosurgery pencil. The support member/socket/connector member 62 includes two vertically aligned openings 64 so that conductive non-cutting ends 26, 28 can be respectively retained in them. An end view of the support member/connector member 62 shown in FIG. 10 showing conductive unconnected non-cutting ends 26, 28 of the ultrapolar electrosurgery blade 10 of the present invention retained within the openings 64 in the support member/socket/connector member 62 is shown in FIG. 11.

A partial top view of another exemplary embodiment of the ultrapolar electrosurgery blade 10 of the present invention showing a sharp cutting end beveled on both sides to create a sharp cutting tip 22 is shown in FIG. 12. A partial perspective view of the exemplary embodiment of the ultrapolar electrosurgery blade 10 of the present invention shown in FIGS. 3 and 7 is depicted in FIG. 13. FIG. 13 clearly shows sharp conductive cutting ends 22, 24 of the top and bottom thin elongated conductive members 12, 14 exposed after coating the top and bottom thin elongated conductive members 12, 14 with non-conductive coating 60 and sharp non-conductive cutting end 74 comprised of the non-conductive coating 60 located between the sharp conductive cutting ends 22, 24. FIG. 13 also clearly shows a portion of the top 66 of the top elongated conductive member 12 exposed between portions of non-conductive coating 60 located on top of the ultrapolar electrosurgery blade 10 and in communication with the sharp cutting end 22 of the top elongated conductive member 12.

FIGS. 14 and 15 are opposing perspective side views of the exemplary embodiment of the ultrapolar electrosurgery blade 10 of the present invention shown in FIG. 7 to further reveal the shape of the ultrapolar electrosurgery blade 10 of the present invention. As shown in FIGS. 14 and 15, the conductive coating 60 which covers most of the top and bottom thin elongated conductive members 12, 14 follows the shape of the top of the top elongated conductive member 12 and the shape of the bottom of the bottom elongated conductive member 14 until it gets to the portions of the top 66 of the top elongated conductive member 12 and the bottom 68 of the bottom elongated conductive member 14 that remain exposed between portions of non-conductive coating on the top of the ultrapolar electrosurgery blade 10 that are located adjacent to the cutting ends 22, 24 of the top and bottom elongated conductive members 12, 14. In addition, as shown in FIGS. 14 and 15, the non-conductive support member/socket/connecting member 62 is designed to retain non-cutting ends 26, 28 of top and bottom elongated conductive members 12, 14 and/or portions of the top and bottom elongated conductive members 12, 14 located near the non-cutting ends 26, 28 to facilitate connection of the ultrapolar electrosurgery blade 10 of the present invention with an electrosurgery pencil. The width of the non-conductive support member/socket/connecting member 62 is greater than a middle width of the ultrapolar electrosurgery blade 10 which is in turn greater than a width of the ultrapolar electrosurgery blade 10 located near the sharp cutting edge of the ultrapolar electrosurgery blade 10 which includes the sharp conductive cutting ends 22, 24 separated by the sharp non-conductive cutting end 74. The ultrapolar electrosurgery blade 10 has a three step configuration along the top and bottom lengths of the blade 10 which relate to the heights of the ultrapolar electrosurgery blade 10.

Figure 16:
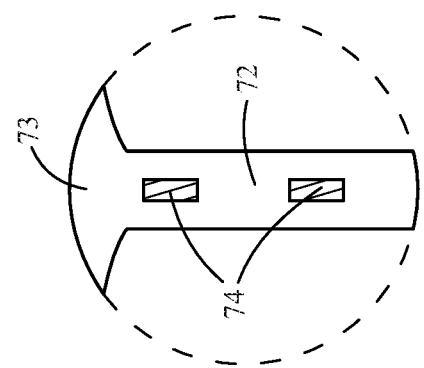
FIGS. 16-17 show different views of an exemplary non-conductive support member/socket/connector member that comprises part of the ultrapolar electrosurgery blade of the present invention when used in a non-telescopic electrosurgery pencil.
Figure 18:
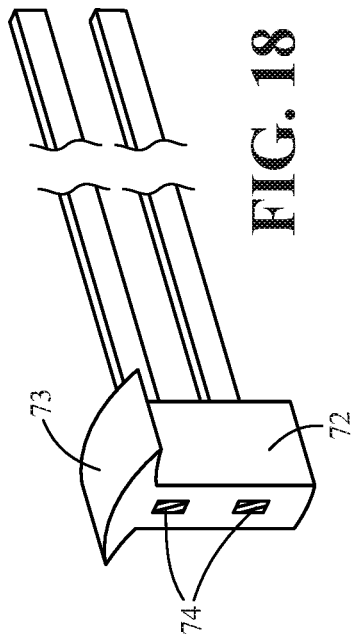
FIGS. 18-19 show different views of an exemplary non-conductive support member/socket/connector member that comprises part of the ultrapolar electrosurgery blade of the present invention when used in a telescopic electrosurgery pencil.
Figure 17:
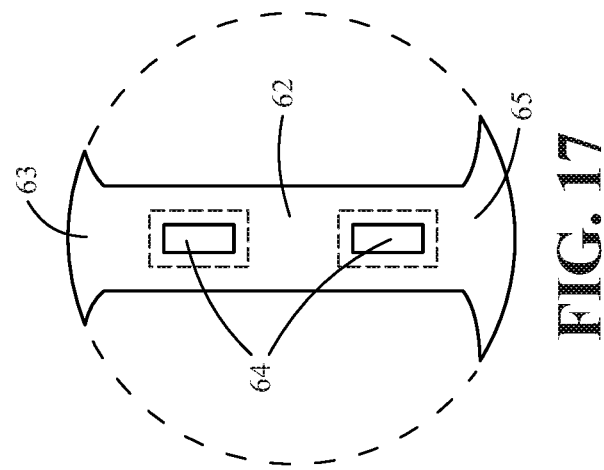
Figure 19:
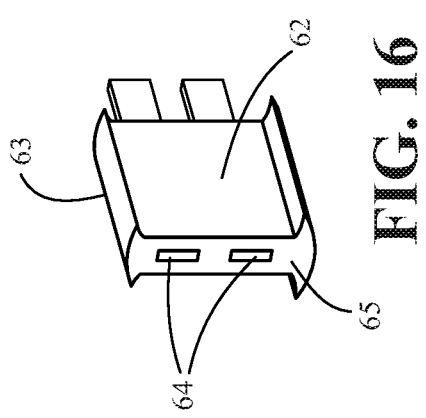

FIGS. 16-17 show different views of an exemplary non-conductive support member/socket/connector member that comprises part of the ultrapolar electrosurgery blade 10 of the present invention when used in a non-telescopic electrosurgery pencil and FIGS. 18-19 show different views of an exemplary embodiment of the non-conductive support member/socket/connector member that comprises part of the ultrapolar electrosurgery blade 10 of the present invention when used in a telescopic electrosurgery pencil. Non-conductive support member/socket/connecting member 62 includes a rounded top portion 63, a rounded bottom portion 65, and two vertically aligned openings 64 for receiving non-cutting ends 26, 28 of top and bottom elongated conductive members 12, 14 and/or portions of the top and bottom elongated conductive members 12, 14 located near the non-cutting ends 26, 28. Non-conductive support member/socket/connecting member 72 includes a rounded top portion 73 and two vertically aligned openings 74 for receiving non-cutting ends 26, 28 of top and bottom elongated conductive members 12, 14 and/or portions of the top and bottom elongated conductive members 12, 14 located near the non-cutting ends 26, 28.

Figure 20:
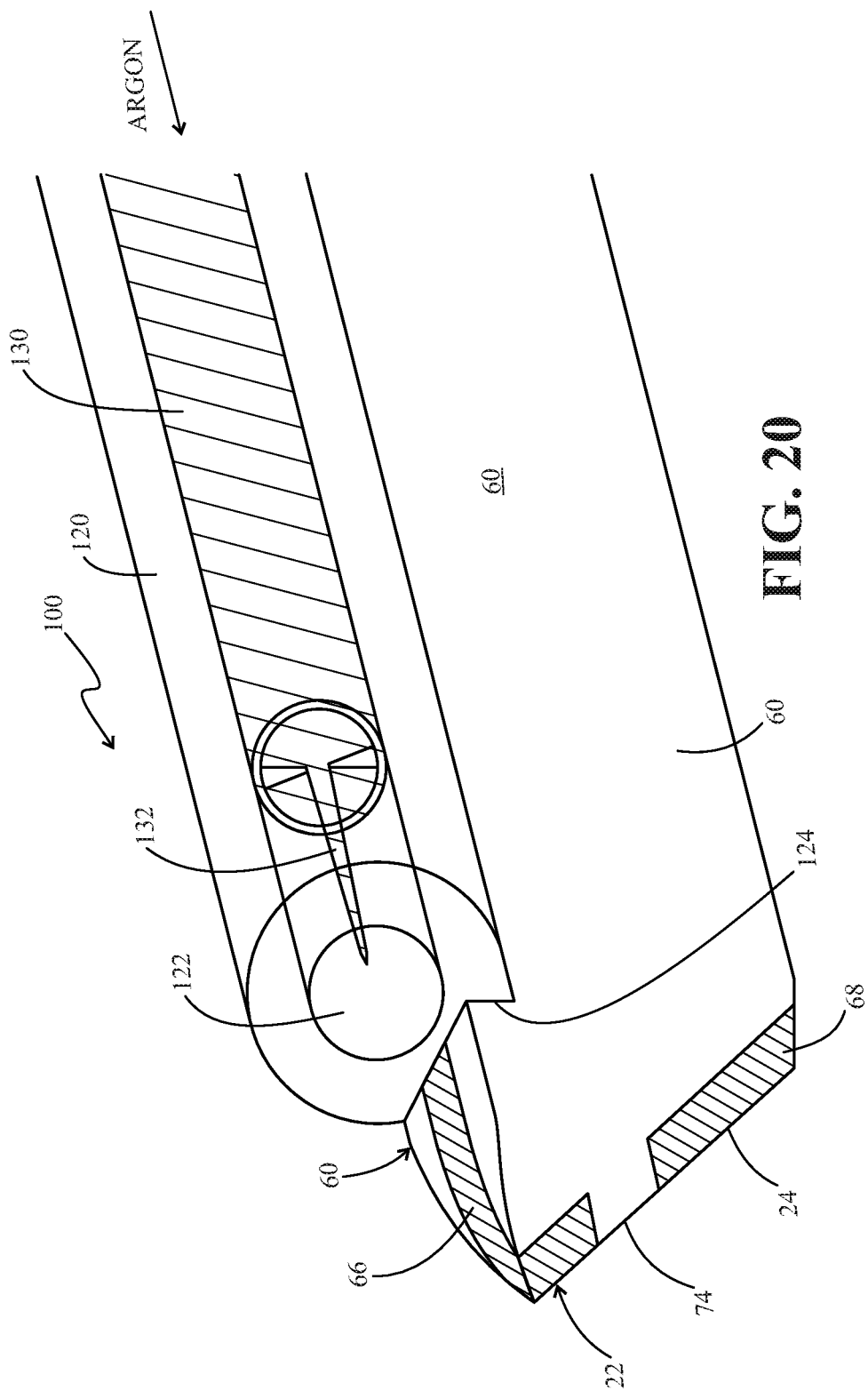
FIG. 20 is a partial perspective view of an exemplary embodiment of the ultrapolar electrosurgery blade assembly of the present invention having argon beam capability for providing argon plasma assisted coagulation.

FIG. 20 is a partial perspective view of an exemplary embodiment of the ultrapolar electrosurgery blade assembly 100 of the present invention having argon beam capability for providing argon plasma assisted coagulation. Ultrapolar electrosurgery blade assembly 100 includes the ultrapolar electrosurgery blade 10 previously described above and further includes a non-conductive tube member 120 having a hollow tubular shaped opening 122 contained therein and a slot 124 where the slot is positioned over a top of the ultrapolar electrosurgery blade 10. The ultrapolar electrosurgery blade assembly 100 further includes a conductive hollow tubular member 130 that is contained within at least a portion of the non-conductive tube member 120. Conductive hollow tubular member 130 may also include a conductive projection 132. The sharp culling edge (comprising conductive cutting ends 22, 26 separated by sharp non-conductive cutting end 74) or a portion of the sharp cutting edge can be used without RF energy for cutting while argon gas is introduced through the conductive hollow tubular member 130 contained within the non-conductive tube member 120 while the conductive hollow tubular member 130 is activated and the conductive projection 132 can direct the ionized argon gas for argon plasma coagulation of tissue. Alternatively, low power may be applied to the ultrapolar electrosurgery blade 10 to coagulate tissue or enhance cutting of tissue while argon gas is introduced through the conductive hollow tubular member 130 contained within the non-conductive tube member 120 while the conducive hollow tubular member 130 is activated and the conductive projection 132 can direct the ionized argon gas for argon plasma coagulation of tissue.

Figure 21:
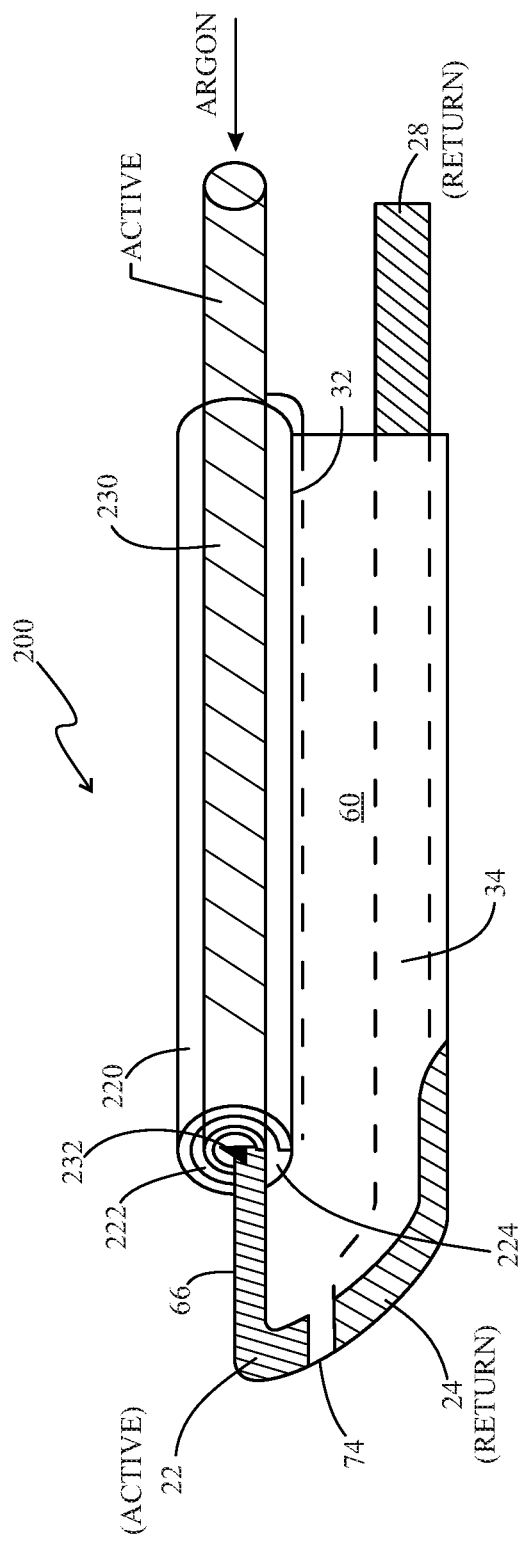
FIG. 21 is a side perspective view of another exemplary embodiment of the ultrapolar electrosurgery blade assembly of the present invention having argon beam capability for providing argon plasma assisted coagulation with the return electrode extending along part of the bottom of the ultrapolar blade.
Figure 22:
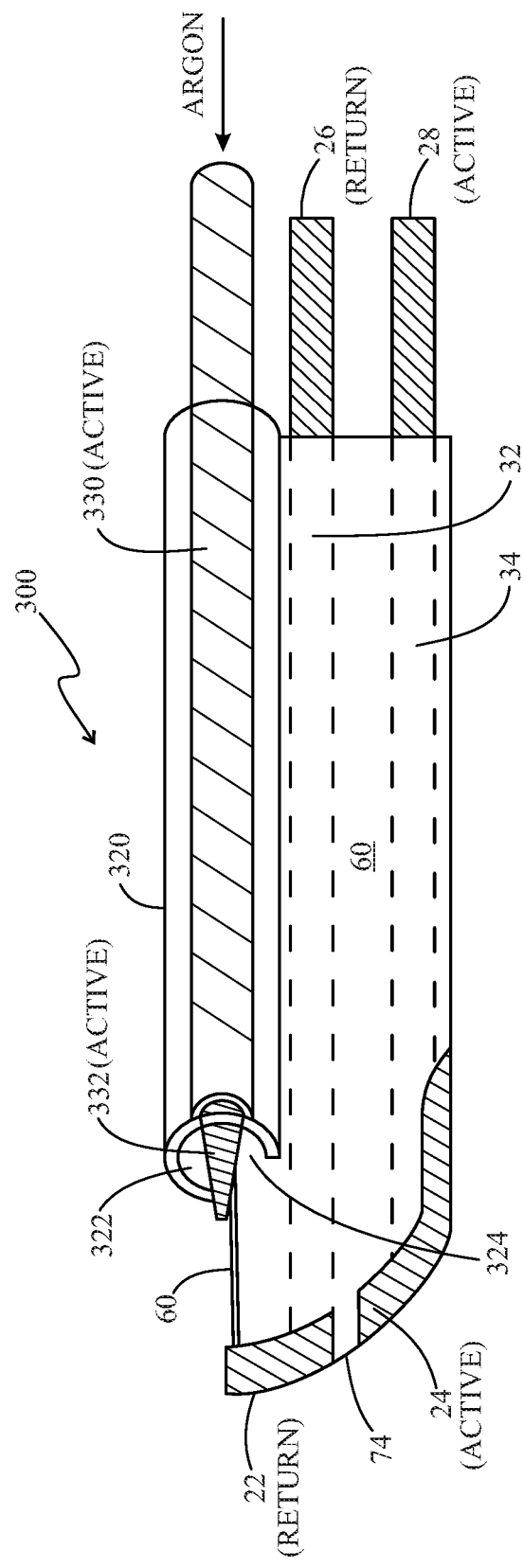
FIG. 22 is a side perspective view of still another exemplary embodiment of the ultrapolar electrosurgery blade assembly of the present invention having argon beam capability which is capable of providing both argon plasma coagulation and argon plasma assisted coagulation.

FIG. 21 is a side perspective view of another exemplary embodiment of the ultrapolar electrosurgery blade assembly 200 of the present invention having argon beam capability for providing argon plasma assisted coagulation with the return electrode extending along part of the bottom of the ultrapolar blade. Ultrapolar electrosurgery blade assembly 200 includes the ultrapolar electrosurgery blade 10 previously described above and further includes a non-conductive tube member 220 having a hollow tubular shaped opening 222 contained therein and a slot 224 where the slot is positioned over a top of the ultrapolar electrosurgery blade 10. The ultrapolar electrosurgery blade assembly 200 further includes a conductive hollow tubular member 230 that is contained within at least a portion of the non-conductive tube member 220. Conductive hollow tubular member 230 may also include a conductive projection 232. The sharp cutting edge (comprising conductive cutting ends 22, 26 separated by sharp non-conductive cutting end 74) or a portion of the sharp cutting edge can be used without RF energy for cutting while argon gas is introduced through the conductive hollow tubular member 230 contained within the non-conductive tube member 220 while the conductive hollow tubular member 230 is activated and the conductive projection 232 can direct the ionized argon gas for argon plasma coagulation of tissue. Alternatively, low power may be applied to the ultrapolar electrosurgery blade 10 to coagulate tissue or enhance cutting of tissue while argon gas is introduced through the conductive hollow tubular member 230 contained within the non-conductive tube member 220 while the conductive hollow tubular member 230 is activated and the conductive projection 232 can direct the ionized argon gas for argon plasma coagulation of tissue thereby employing argon plasma assisted cutting and/or coagulation FIG. 22 is a side perspective view of still another exemplary embodiment of the ultrapolar electrosurgery blade assembly 300 of the present invention having argon beam capability which is capable of providing both argon plasma coagulation and argon plasma assisted coagulation. Ultrapolar electrosurgery blade assembly 300 includes the ultrapolar electrosurgery blade 10 previously described above and further includes a non-conductive tube member 320 having a hollow tubular shaped opening 322 contained therein and a slot 324 where the slot is positioned over a top of the ultrapolar electrosurgery blade 10. The ultrapolar electrosurgery blade assembly 300 further includes a conductive hollow tubular member 330 that is contained within at least a portion of the non-conductive tube member 320. Conductive hollow tubular member 330 may also include a conductive projection 332. In this embodiment of the ultrapolar electrosurgery blade assembly 300, an exposed portion of the return electrode 22 of the ultrapolar electrosurgery blade 10 is positioned near the top of the electrosurgery blade 10 such that it is in alignment with the conductive hollow tubular member 330, through which the argon gas is introduced, and the conductive projection 332 extending from an end of the conductive tubular member 332 so that a complete circuit is formed to ionize the argon gas for argon plasma coagulation. The ultrapolar electrosurgery blade assembly 300 of the present invention is also capable of cutting a patient's tissue using the sharp cutting edge (comprising conductive cutting ends 22, 26 separated by sharp non-conductive cutting end 74) of the ultrapolar electrosurgery blade 10 alone without any use of RF energy and without any use of argon plasma. The ultrapolar electrosurgery blade assembly 300 of the present invention can also enhance the cutting of a patient's tissue using the sharp conductive cutting edges 22, 24 of the ultrapolar electrosurgery blade 10 by also supplying RF energy to the exposed portion of the active electrode 24 of the ultrapolar electrosurgery blade 10. Moreover, the ultrapolar electrosurgery blade assembly 300 of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar electrosurgery blade 10 can be used without any RF energy for cutting while the conductive hollow tubular member 330 through which the argon gas is introduced, and which is contained within the non-conductive tube member 320, is activated and directed via conductive projection 332 to provide ionized argon gas for argon plasma coagulation of tissue. In another example, low power may be applied to the ultrapolar electrosurgery blade 10 to coagulate tissue or enhance cutting of tissue while the conductive hollow tubular member 330 through which the argon gas is introduced, and which is contained within the non-conductive tube member 320, is activated and directed via the conductive projection 332 to provide ionized argon gas for argon plasma coagulation of tissue.

The drawings and description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar electrosurgery blade comprising:
a top thin elongated conductive member and a bottom thin elongated conductive member each having opposing planar sides with each opposing planar side having a length and a width, a sharp cutting end, and an opposite non-cutting end wherein the top and bottom thin elongated conductive members are in vertical alignment with one another and spaced apart from one another along more than half of their lengths by a same width that is smaller than the width of each of the opposing planar sides of the top and bottom thin elongated conductive members located adjacent to the sharp cutting ends; and
a nonconductive coating that covers both opposing planar sides of the top and bottom thin elongated conductive members and that fills the space located between the top and bottom thin elongated conductive members wherein at least a portion of the sharp cutting ends of the top and bottom thin elongated conductive members and their opposite non-cutting ends remain exposed.

2. The ultrapolar electrosurgery blade of claim 1 further comprising a non-conductive support member having two openings therein in vertical alignment with one another wherein a portion of said top and bottom thin elongated conductive members are respectively contained within one of the two openings.

3. The ultrapolar electrosurgery blade of claim 2 wherein the non-conductive support member comprises a ceramic material.

4. The ultrapolar electrosurgery blade of claim 1 wherein the non-conductive coating covers at least a portion of a top of the top thin elongated conductive member and at least a portion of a bottom of the bottom thin elongated conductive member.

5. The ultrapolar electrosurgery blade of claim 1 wherein at least a portion of a top of the top thin elongated conductive member is exposed between portions of non-conductive coating located on the opposing planar sides of the top thin elongated conductive member and at least a portion of a bottom of the bottom thin elongated conductive member is exposed between portions of non-conductive coating located on the opposing planar sides of the bottom thin elongated conductive member.

6. The ultrapolar electrosurgery blade of claim 1 wherein the top and bottom thin elongated conductive members comprise a hard metal.

7. The ultrapolar electrosurgery blade of claim 1 wherein the non-conductive coating comprises a ceramic material.

8. The ultrapolar electrosurgery blade of claim 1 wherein the ultrapolar electrosurgery blade has a sharp cutting edge comprising the sharp cutting ends of the top and bottom thin elongated conductive members separated by a sharp non-conductive cutting end.

9. An ultrapolar electrosurgery blade assembly having argon beam capability that includes the ultrapolar electrosurgery blade of claim 1 and further comprises:
a non-conductive tube member having a hollow tubular shaped opening contained therein and a slot wherein the slot is positioned over a top of the ultrapolar electrosurgery blade such that the slot is in physical contact with the ultrapolar electrosurgery blade; and
a conductive hollow tubular member contained within at least a portion of the non-conductive tube member wherein an argon gas is capable of being introduced through the conductive hollow tubular member.

10. The ultrapolar electrosurgery blade assembly of claim 9 wherein at least a portion of a top of the top thin elongated conductive member is exposed between portions of the non-conductive coating located on the opposing planar sides of the top thin elongated conductive member and contained within the non-conductive tube member and the ultrapolar electrosurgery blade assembly further comprises a conductive projection extending from at least one of the conductive hollow tubular member contained within the non-conductive tube member and the portion of the top of the top thin elongated conductive member that is exposed between portions of the non-conductive coating located on the opposing planar sides of the top thin elongated conductive member and contained within the non-conductive tube member.

11. The ultrapolar electrosurgery blade assembly of claim 9 wherein the non-conductive coating covers a top of the top thin elongated conductive member located between the conductive hollow tubular member and the exposed cutting end of the top thin elongated conductive member and the ultrapolar electrosurgery blade assembly further comprises a conductive projection extending from an end of the conductive hollow tubular member contained within the non-conductive tube member.

12. The ultrapolar electrosurgery blade assembly of claim 9 further comprising a non-conductive support member having two openings therein in vertical alignment with one another wherein a portion of said top and bottom thin elongated conductive members are respectively contained within one of the two openings.

13. The ultrapolar electrosurgery blade assembly of claim 9 wherein the ultrapolar electrosurgery blade has a sharp cutting edge comprising the sharp cutting ends of the top and bottom thin elongated conductive members separated by a sharp non-conductive cutting end.

14. The ultrapolar electrosurgery blade assembly of claim 13 wherein at least a portion of a top of the top thin elongated conductive member is exposed between portions of non-conductive coating located on the opposing planar sides of the top thin elongated conductive member and at least a portion of a bottom of the bottom thin elongated conductive member is exposed between portions of non-conductive coating located on the opposing planar sides of the bottom thin elongated conductive member.

15. The ultrapolar electrosurgery blade assembly of claim 9 wherein the conductive hollow tubular member comprises a hard metal.

16. The ultrapolar electrosurgery blade assembly of claim 9 wherein the non-conductive tube member comprises a ceramic.

17. The ultrapolar electrosurgery blade assembly of claim 9 wherein the non-conductive coating of the ultrapolar electrosurgery blade comprises a ceramic.

18. The ultrapolar electrosurgery blade assembly of claim 9 wherein the top and bottom thin elongated conductive members of the ultrapolar electrosurgery blade comprise a hard metal.

19. The ultrapolar electrosurgery blade of claim 9 wherein the conductive hollow tubular member contained within the non-conductive tube member comprises a slot wherein the slot of the conductive hollow tubular member is also positioned over at least a portion of the top of the ultrapolar electrosurgery blade such that the slot is in physical contact with the ultrapolar electrosurgery blade.

20. An ultrapolar electrosurgery blade comprising:
a top thin elongated conductive member and a bottom thin elongated conductive member each having opposing planar sides with each of the opposing planar sides having a length and a width, a sharp cutting end, and an opposite non-cutting end wherein the top and bottom thin elongated conductive members are in vertical alignment with one another and spaced apart from one another along more than half of their lengths by a same width that is smaller than the width of each of the opposing planar sides of the top and bottom thin elongated conductive members located adjacent to the sharp cutting ends; and
a non-conductive housing containing both opposing planar sides of the top and bottom thin elongated conductive members and the space located between the top and bottom thin elongated conductive members.

\* \* \* \* \*